United States Patent [19]

Hooreman

[11] Patent Number: 5,047,240

[45] Date of Patent: Sep. 10, 1991

[54] METHOD FOR PRODUCING A PROTEOLYTIC COMPLEX STIMULATING THE ACTIVITY OF THE PANCREAS AND ITS APPLICATION IN ZOOTECHNY

[76] Inventor: Michel Hooreman, 10, rue du Delta, F-75009 Paris, France

[21] Appl. No.: 187,540

[22] PCT Filed: Jun. 19, 1987

[86] PCT No.: PCT/FR87/00233

§ 371 Date: Apr. 18, 1988

§ 102(e) Date: Apr. 18, 1988

[87] PCT Pub. No.: WO87/07905

PCT Pub. Date: Dec. 30, 1987

[51] Int. Cl.$^5$ .................. A61K 37/54; C12N 9/52; A23K 1/165

[52] U.S. Cl. .................. 424/94.63; 435/71.2; 435/223; 435/814; 435/896; 426/2; 426/801; 426/807

[58] Field of Search .................. 424/94.63; 435/71.2, 435/223, 814, 896; 426/2, 801, 807

[56] References Cited

U.S. PATENT DOCUMENTS 3,683,069  8/1972  Hooreman ........................ 435/896
3,823,072  7/1974  Hooreman ........................ 435/896
4,038,419  7/1977  Ferns ............................. 435/896

FOREIGN PATENT DOCUMENTS 1133579  11/1968  United Kingdom .

OTHER PUBLICATIONS

Shishkova et al., Chem. Abstracts, vol. 94: 204352s (1981).
Rassulin et al., Chem. Abstracts, vol. 94:204353t (1981).
Williamson et al., Biochimica et Biophysica Acta, 543 (1978), 397–402.
Kokubu et al., Biotechnol. Bioeng., vol. 13(1981) pp. 29–39.

*Primary Examiner*—Jacqueline Stone
*Attorney, Agent, or Firm*—Bierman and Muserlian

[57] ABSTRACT

Method for producing a proteolytic complex formed after cultivation of a strain of *Streptomyces fradiae* while maintaining the pH of the culture medium between 7 and 7.5, and extracting said complex by filtration in the presence of a clarifying agent and ultrafiltration on a specific membrane and finally atomization; the invention also relates to the new proteolytic complex thus obtained and its applications in zootechny due to its stimulating effect on the activity of the pancreas.

11 Claims, No Drawings

METHOD FOR PRODUCING A PROTEOLYTIC COMPLEX STIMULATING THE ACTIVITY OF THE PANCREAS AND ITS APPLICATION IN ZOOTECHNY

In the French Patent No. 2,034,559, the applicant described a process for producing proteolytic complexes starting from *Streptomyces fradiae*, and the possible use of such complexes especially in zootechny.

Experiments showed that the results obtained when the process of this patent is performed are generally positive but irregular or insufficient, so that the uses of such complexes remained very restricted.

The present application provides a process which enables one to obtain a new complex particularly having a more precisely stated composition and to define the conditions which allow this new complex to give with regularity some important improvements in zootechny.

The present application also provides the new proteolytic complex obtained according to this process.

In the English Patent No. 1,133,579, SHIONOGI mentioned that *Streptomyces fradiae* produces at least 5 proteases, named: Ia, Ib, II, III, IV and 2 peptidases. The applicant also obtained, starting from *Streptomyces fradiae*, some enzymes, which, having practically the same general properties, are of the same type as those described in the above SHIONOGI's Patent. So, in the present application, for the clarity of the language, the enzymes are designated with the same Roman numerals as those used in the said SHIONOGI's Patent.

The applicant observed that complexes which are exclusively composed with proteases of type II, III, IV give a moderate reduction of the intestinal mucus viscosity prescribed in its initial patent and generally give positive results in zootechny, but irregular or insufficient; Among all these complexes, only the particular complex, characterized by a greater abundance of protease of type II with regard to proteases of type III or IV, may regularly give an important improvement of zootechnic performance.

The applicant also observed that global complexes composed of the 5 types of proteases and the 2 types of peptidases, causes an excessive reduction of the intestinal mucus viscosity and are aggressive for the mucus of the membrane; they are then unusable in zootechny.

It is this reason why the applicant tried to obtain the particular complex exclusively composed of proteases of type II, III, IV with preponderance of protease of type II which is the object of claims 5 to 7 of the present application.

Process of Production

The complex, according to the invention, is obtained under the following conditions:

Fermentation

There is used a *Streptomyces fradiae* strain, for example the typical WASKMAN 3535 strain, filed at American Type Culture Collection (in abbreviated form: A T C C) under the number : 10,745. This strain may be periodically regenerated by the classic technique of dissociation on gelosed medium to eliminate possible spontaneous mutants having a low proteolytic activity. This strain may also be improved by the classic technique of induced mutation in order to obtain an increase of the proteolytic activity.

To prepare precultures of this strain, first in stirred flasks, then in an intermediate fermentor which is then inoculated in the fermentor of industrial production. The production medium may be composed as follows: soybean meal 15 g/l, glucose 30 g/l, bipotassium phosphate 1 g/l, and calcium carbonate 10 g/l. After sterilization, the pH is about 7.0. The temperature of fermentation is maintained at 28° C. and the sterile air at 0.3 volume per volume of the medium per minute.

The pH of the medium, initially near 7.0, starts to decrease and reaches 6.5 after about 10 hours of fermentation; it increases then quickly and reaches 7.5 after about 20 hours of fermentation, then it continues to increase more slowly to finally reach 8.2.

There has been observed that it was very important to maintain the pH between 7.5 and 7.0 with an automatic addition of an acidic solution, for example, a 3N hydrochloric acid solution, which allows:

to avoid the fragmentation of mycelium and the release, in the medium, of some secondary metabolites, proteases of type Ia, Ib and peptidases. These secondary metabolites and these enzymes so remain endocellular.

to increase the production of proteases of type II, III, IV which are principally exocellular enzymes.

to obtain a particularly important increase for production of protease of type II. The fermentation time may vary from 72 to 96 hours, and the final titer of the medium is about 15,000 Anson Units/ml, it lies much beyond the titer of 3,000 Anson Units/ml as mentioned in the French Patent No. 2,034,559.

An Anson Unit (in abbreviated form : A.U) is here defined as the quantity of enzyme which, incubated for 10 minutes at 25° C. and at pH 7.5, in the presence of denaturated hemoglobin, releases from this substrate, the equivalent of 1 $\mu$g of tyrosin determined by spectrophotometic absorption at 280 nm on the filtrate unprecipitable with trichloroacetic acid.

Extraction

The mycelium is separated from the production medium by a clarifying filtration.

The complex, instead of being extracted by the classic techniques for separating of the enzymes (successive precipitations, passing over a column) is extracted by a more recent technique ultrafiltration.

The ultrafiltration membranes which may give the best yields are researched. The membranes having a cutting threshold corresponding to a molecular weight of 30,000 are not suitable because they allow more than 50% of the complex to go out. The membranes having a cutting threshold corresponding to a molecular weight of 1,000, are not suitable because they do not allow the separation of the complex from some secondary metabolites having a low molecular weight. There was finally observed that it was suitable to use some membranes having a cutting threshold corresponding to a molecular weight within the range of from 2,000 to 12,000. There may be used, for example, the polysulfone membrane sold by the Society MILLIPORE under the name P.T.G.C, the cutting threshold of which corresponds to a molecular weight of 10,000.

The concentrate obtained has been treated by atomization.

The complex is finally obtained in the form of a clear beige powder titrating at least 2,000 A.U/mg, the inert supports, for example superdried starch, optionally added before or after atomization, being not taken into consideration.

The total yield in proteolytic activity, which is about 70% is higher than the one which may be obtained industrially by successive precipitations or passing over a column.

IN BRIEF

It is suitable, to obtain the desired proteolytic complex starting from a *Streptomyces fradiae* strain, to maintain the pH of the culture medium within the range of from 7.5 to 7.0 by adding an inorganic or organic acid solution, then to perform the extraction of the proteolytic complex by filtration in the presence of a clarifying agent then ultrafiltration with a membrane having a cutting threshold corresponding to a molecular weight within the range of from 2,000 to 12,000, and finally atomization.

It is particularly convenient to use as *Streptomyces fradiae* strain the typical WASKMAN 35354 strain filed at ATCC under the number 10,745 maintaining the pH of the culture medium within the range of from 7.5 to 7.0 by the means of a 3N hydrochloric acid solution, and using as ultrafiltration membrane, a polysulfone-containing membrane sold by the Company MILLIPORE under the name P.T.G.C.

Characteristics of this new complex presence (determined by enzymo-electrophoresis) of proteases of type II, III, IV to the exclusion of proteases of type Ia, Ib and peptidases preponderance of protease of type II which represents at least 40% of the total proteolytic activity, proteases of type III or IV representing at most each 30% of this total activity.

Characteristics of the proteases constituting this new complex

Protease of type II :
molecular weight about 18,000;
isoelectric point about 9.0;
by electrophoresis at pH 8.0,
displacement towards the cathode at a relatively low speed Protease of type III :
molecular weight about 14,000;
isoelectric point about 9.0;
by electrophoresis at pH 8.0,
displacement towards the cathode at medium speed Protease of type IV :
molecular weight about 16,500;
isoelectric point about 9.0;
by electrophoresis at pH 8.0,
displacement towards the cathode at a relatively high speed

Applications in zootechny

The applications in zootechny of the complex of the invention give the best results when they are performed as follows:

Use of foods having a high content of raw proteins

There was observed that the growth of animals was stimulated by the complex tending to privilege the protein-genesis compared with the lipogenesis. For example, there was observed that the dead bodies of treated calves and pigs were sometimes better classified because they have more muscles and less fat, but these improvements were irregular.

It was then inferred that this tendency of the complex to stimulate the protein anabolism could only be totally obtained when the feed used had a sufficient content of raw proteins. It was effectively confirmed by experiments that to obtain, with regularity, a valuable stimulation of protein anabolism, one of the conditions to observe was to use a feed with a rather high raw protein content, viz having a high content of total nitrogenous matter (in abbreviated form: T.N.M).

For example, this content in T.N.M. has to be:
≧23% for feeds intended for the starting growth of chickens
≧22% for feeds of suckling for calves or lambs
≧20% for feeds of weaning for piglets
≧16% for the only food intended for sows in period of gestation or lactation.

The use of such foods does not generally correspond to the usual practice because:

the animals are not always able to assimilate completely a food having a high T.N.M. level the undigested proteins may then provoke a lack of balance of the intestinal flora by an excessive development of proteolytic bacterias and an increase of the frequency of diarrheas. These risks are suppressed when using the complex because animals are then allowed to assimilate effectively foods having a high T.N.M. level foods having a high T.N.M. level are more expensive then ordinary foods and then prices are still increase by further addition of the complex. Nevertheless, this increase may be compensated by the fact that the complex allow the use of foods, the energy level of which is lower than the usual standards. In any case, owing to the important improvement of the so-obtained zootechnic performance data, the total economical balance of the operation remain very advantageous.

Use of foods intended for mammals in period of pregnancy, lactation (or suckling) and weaning There was observed that the particular complex, described in the present application, stimulates the exocrine activity of the pancreas, which is new with regard to the French Patent No. 2,034,599. This stimulation is shown especially in experiments on the rats during which it was observed an important increase of the intrapancreatic concentration of all the enzymes excreted by the pancreatic canal, this increase may reach 50% for amylase, 70% for trypsinogen and chymotrypsinogen, 80% for lipase. Therefore, the special complex, as described in the present application, may be considered as a new substance having new and unexpected properties.

Due to this stimulation of the exocrine activity of the pancreas, it was inferred that the complex was particularly effective when pancreas may be deficient (case of pregnant females) and when it had to give an exceptional producing work (case of females suckling a large litter)or an exceptional adaptation work (case of young mammals during weaning period). The following examples corroborate this working hypothesis:

a) The pancreas of females at the end of pregnancy is often deficient because of the important increase of the uterus volume compresses all the digestive organs. By adding the complex to the food given to such females, a good function of pancreas is restored and an increase of the weight of the letter, at binter, is obtained.

For example, with a single food for pregnant or suckling having a T.N.M. level of 16%, an addition of complex at the dose of 120 A.U/g of food gives an increase of 17% of the weight of litters, at birth : 15 kg instead of 12.8 kg (10.7 piglets of 1.4 kg instead of 10.2 piglets of 1.25 kg).

b) The daily food consumption of females suckling a large litter has to increase quickly : between the end of pregnancy and the 8th day of suckling, it has to be multiplied by 2.5 (about 45 g instead of 18 g for the rats, 350 g instead of 140 g for female rabbits, 6 kg instead of 2.4 for sows). The pancreas of these suckling females have to furnish a considerable additional work, and it is precisely in these conditions that the action of the complex is the more significant.

For example, with a single food for pregnant or suckling sows having a T.N.M. level of 17%, an addition of complex at the dose of 120 A.U/g of food gives an increase of 25% of the weight of litters with a weaning at 21 days : 54 kg instead of 43 kg (9.4 piglets of 5.7 kg instead of 9.1 piglets of 4.7 kg).

In another experiment performed in similar conditions, but with a weaning at 28 days instead of 21 days, the increase of the weight of litters is also about 25% : 52 kg instead of 41 kg at 21 days (9.7 piglets of 5.4 kg instead of 8.5 piglets of 4.8 kg) and 69 kg instead of 55 kg with a weaning at 28 days (9.7 piglets of 7.1 kg instead of 8.5 piglets of 6.5 kg).

This increase of the weight of litters goes on a par with a decrease of food consumption necessary to maintain the sows in a good condition, decrease which, for a whole year, is about 10% (about 1,000 kg instead of 1,100 kg).

c) During the weaning, young mammals have to pass from the consumption of maternal milk to the one of combined foods and the pancreas has to adapt itself quickly to this important change. The addition of the complex in these combined foods allows then to make this adaptation easier. For example, with a weaning food for piglets between 5 an 10 kg, having a T.N.M. level of 23%, an addition of complex at a dose of 120 A.U/g of food gives an increase of 15% of the daily average weight (216 g instead of 188 g) and a decrease of 15% of the consumption index (1.59 instead of 1.83).

Still more than in the case of piglets, the action of the complex at the moment of weaning may be more important for young rabbits and young ruminants (kids, lambs, calves). For these animals, the increase of the gain of the daily average weight, when using the complex, may reach 40% (47 g instead of 33 g during the week following the weaning of 5 weeks old young rabbits 797 g instead of 523 g during the month following the weaning of 2 months old calves).

Definitions of the extreme usable doses

There was observed that, to give the regularly important improvements, the complex may be used at a dose within a rather narrow range, viz at a dose within the range of from to 160 A./U per g of foods.

In the case of feeding of suckling sows, the used dose is of A.U per g of foods and the increase of the weight of litters of piglets weaned at 21 days is about 25%. If this dose is fixed at 200 A.U. per g, the increase of this weight is not more than 4% : 49 kg instead of 47 kg, or 8.2 piglets of 6.0 kg instead of 8.4 piglets of 5.6 kg.

In the case of feeding of piglets, the used dose is of 120 A.U per g and the improvement of the zootechnic performance data is 15%. With a dose of 200 A.U per g, the increase of the performance date becomes irregular : at the best, it remains 15% after 3 weeks of testing, but becomes nil after 5 weeks of testing.

What I claim is:

1. A process for producing an enzymatic complex by fermentation of a strain of *Streptomyces fradiae* which consists in keeping the pH value within the range of from 7.0 to 7.5 during the culture by adding an inorganic acid or organic acid solution, separating the broth from the mycelium by filtration with a clarifying agent, and fractionating the resulting filtrate by ultrafiltration with a membrane having a cutting threshold corresponding to a molecular weight within the range of from 2,000 to 12,000 and finally atomizing this enzymatic mixture to obtain a proteolytic complex consisting essentially of proteases of type II, III, and IV, in which at least 40% of the proteolytic activity is afforded by protease of type II, and in which the proteases of type III and IV each give at the most 30% of the total proteolytic activity.

2. A process according to claim 1 wherein the *Streptomyces fradiae* strain is the typical WAKSMAN 3535 strain filed at A.T.C.C. under the number 10,745.

3. A process according to claim 1 wherein the pH of the culture medium is kept constant during fermentation by adding a 3N hydrochloric acid solution.

4. A process according to claim 1 wherein the ultrafiltration membrane is a polysulfone membrane.

5. A proteolytic complex consisting essentially of proteases II, III, IV in which at least 40% of the proteolytic activity is afforded by protease of type II, and in which proteases of type III and IV each give at the most 30% of the total proteolytic activity prepared by the process of claim 1.

6. The proteolytic complex according to claim 5 having a proteolytic titer of at least 2,000 Anson Units/mg.

7. A method of improving the feeding of animals comprising incorporating into the animal feed, a weight increasing amount of the proteolytic complex of claim 5.

8. A method of increasing the weight of weaning young mammals or pregnant or suckling females comprising incorporating into the animal feed an amount of the proteolytic complex of claim 2 in an amount sufficient to increase the weight of the said animals.

9. The method of claim 8 wherein the animals are pregnant or breast feeding rabbits.

10. The method of claim 8 wherein the animals are sows.

11. The method of claim 8 wherein the animals are weaning or post-weaning piglets.

* * * * *